US012594335B2

(12) United States Patent
Yang et al.

(10) Patent No.: US 12,594,335 B2
(45) Date of Patent: Apr. 7, 2026

(54) PLATINUM-BASED DRUG-/PHOTOSENSITIZER-LOADED PROTEIN NANOPARTICLE, AND PREPARATION METHOD THEREFOR AND APPLICATION THEREOF

(71) Applicant: SOOCHOW UNIVERSITY, Suzhou (CN)

(72) Inventors: Hong Yang, Suzhou (CN); Tao Xu, Suzhou (CN); Huabing Chen, Suzhou (CN); Miya Zhang, Suzhou (CN); Liang Chen, Suzhou (CN); Yibin Deng, Suzhou (CN); Jialu Yao, Suzhou (CN); Jiali Luo, Suzhou (CN); Yanhua Zhai, Suzhou (CN)

(73) Assignee: SOOCHOW UNIVERSITY, Suzhou (CN)

(*) Notice: Subject to any disclaimer, the term of this patent is extended or adjusted under 35 U.S.C. 154(b) by 565 days.

(21) Appl. No.: 18/012,295

(22) PCT Filed: Jul. 24, 2020

(86) PCT No.: PCT/CN2020/104637

§ 371 (c)(1),
(2) Date: Jul. 9, 2023

(87) PCT Pub. No.: WO2022/016555

PCT Pub. Date: Jan. 27, 2022

(65) Prior Publication Data

US 2023/0364239 A1 Nov. 16, 2023

(51) Int. Cl.

| | |
|---|---|
| ***A61K 41/00*** | (2020.01) |
| ***A61K 9/51*** | (2006.01) |
| ***A61K 33/243*** | (2019.01) |
| ***A61P 35/00*** | (2006.01) |

(52) U.S. Cl.

CPC ........ *A61K 41/0061* (2013.01); *A61K 9/5169* (2013.01); *A61K 33/243* (2019.01); *A61P 35/00* (2018.01)

(58) Field of Classification Search

CPC ...... A61K 9/5169; A61K 33/243; A61P 35/00

See application file for complete search history.

(56) References Cited

U.S. PATENT DOCUMENTS 5,871,710 A * 2/1999 Bogdanov .............. A61K 47/56
424/9.34

FOREIGN PATENT DOCUMENTS

| | | | |
|---|---|---|---|
| CN | 104189916 A | | 12/2014 |
| CN | 109730998 A | * | 5/2019 |
| CN | 110368374 A | | 10/2019 |

OTHER PUBLICATIONS

CN109730998A machine translation, 2019, pp. 1-23 (Year: 2019).*

Shi, H. et al. "Pharmacokinetic study of a novel sonosensitizer chlorin-e6 and its sonodynamic anti-cancer activity in hepatoma-22 tumor-bearing mice" Biopharm & Drug Disp, 2011, 32 (6), 319-332 (Year: 2011).*

Dehong Hu et al., "Activatable albumin-photosensitizer nanoassemblies for triple-modal imaging and thermal-modulated photodynamic therapy of cancer" Biomaterials 93 (2016) 10-19 (Mar. 31, 2016).

Mihaela N. Mocanu et al., "Ultrasound-assisted interaction between chlorin-e6 and human serum albumin: pH dependence, singlet oxygen production, and formulation effect" Spectrochimica Acta Part A: Molecular and Biomolecular Spectroscopy 190 (2018) 208-214 (Sep. 13, 2017).

* cited by examiner

*Primary Examiner* — Andrew S Rosenthal

(74) *Attorney, Agent, or Firm* — SZDC Law PC

(57) ABSTRACT

A platinum-based drug/photosensitizer-loaded protein nanoparticle, and a preparation method therefor and an application thereof. The platinum-based drug/photosensitizer-loaded protein nanoparticle includes a platinum-based drug/photosensitizer complex, and a protein that encapsulates the platinum-based drug/photosensitizer complex. The prepared nanoparticles have a small particle size, are evenly dispersed and round in shape, and have good chemical stability, light stability, and high active oxygen generation capability when irradiated by near-infrared light; in cell experiments and animal experiments, it is verified that strong cytotoxicity to tumor cells and good in vivo tumor targeting are achieved, a synergistic effect is exerted, toxic and side effects are reduced, the use of chemotherapy and photodynamic therapy in combination to treat tumors is achieved, and metastasis of tumors is inhibited.

6 Claims, 10 Drawing Sheets

PLATINUM-BASED DRUG-/PHOTOSENSITIZER-LOADED PROTEIN NANOPARTICLE, AND PREPARATION METHOD THEREFOR AND APPLICATION THEREOF

FIELD OF THE INVENTION

The present invention relates to the preparation of a platinum-based drug/photosensitizer-loaded albumin nanoparticle with dual therapeutic effects, the albumin nanoparticle being used as a new formulation of anti-tumor drug to achieve combined treatment of tumors and inhibit tumor metastasis.

BACKGROUND OF THE INVENTION

A malignant tumor is a serious disease that threatens human health. In clinical treatment, both treatment and inhibition of metastasis are required.

At present, a variety of materials have been studied as a nano drug-loaded system. Nanomaterials prepared with biomacromolecule proteins as carriers have the advantages of being well biocompatible, safe and non-toxic. The carrier materials of a drug can selectively target the drug to a lesion site, thus effectively reducing the toxic and side effects of the drug on normal tissues. Therefore, the carrier materials have an important position and research value in the pharmaceutical research of nano drug carriers and anti-tumor drugs.

Albumin is the most abundant protein in plasma. Human serum albumin (HSA) is an albumin whose structure is the most clearly known at present, and the molecular weight is 66 kD. A non-glycosylated single-chain polypeptide contains 585 amino acids, and isoelectric points are range from 4.7 to 4.9 of the acidic protein. It is easily soluble in water, its concentration is 42 g/L in plasma, accounting for about 60% of total plasma proteins.

Platinum-based drugs have been studied for more than 50 years. In 1965, American scholars Rosenberg et al. accidentally found that cisplatin complexes can inhibit cell proliferation and can be used as anti-tumor drugs. Since then, the platinum-based drugs have rapidly attracted people's attention, and the research on platinum-based anti-tumor drugs has also become a hot spot. Up to now, the platinum-based drugs have developed to the fourth generation, among which cisplatin, carboplatin and oxaliplatin have been used clinically. An important precursor for the synthesis of these platinum-based drugs is diammine dihydrate platinum nitrate, so the diammine dihydrate platinum ion is also called a cisplatin precursor ion. Cisplatin (also known as cis-dichlorodiammine platinum (II), or CDDP for short), as a classical platinum-based anti-tumor drug, plays an important role in tumor chemotherapy. A cisplatin anti-cancer spectrum and its application range are very wide. The cisplatin anti-cancer spectrum is mainly used clinically in the treatment of testicular cancer, ovarian cancer, bladder cancer, head and neck cancer, esophageal cancer, and small-cell lung cancer. When combined with doxorubicin, paclitaxel and 5-fluorouracil (5-Fu), it can be used to treat head and neck cancer and gastric cancer. However, its high-dosage and long-term use in clinical practice is limited by its severe toxic and side effects, low solubility, and drug tolerance.

Photodynamic therapy (PDT) in tumor treatment is a new technology that uses a photodynamic reaction to diagnose and treat diseases after uptake of photosensitizers by tumor tissues. PDT has three important factors: an excitation light source, a photosensitizer, and reactive oxygen. Its mechanism is as follows: Photosensitizer molecules absorb the energy of photons of the light with the corresponding wavelength, thereby changing from a ground state to a singlet excited state; the photosensitizer molecules in the excited state can return to the ground state through a physical de-excitation process, thereby generating fluorescence for clinical diagnosis, namely fluorescence diagnosis; the photosensitizer molecules can also be converted to a triplet excited state, thus transferring energy to adjacent molecular oxygen to produce reactive oxygen species (ROS), which can induce autophagy, apoptosis and necrosis of cells in target organs.

Because the derivatives of "chlorophyll a" have a high extinction coefficient and a high singlet oxygen quantum yield in the red-light region, they have been widely used as photosensitizers. Among them, Ce6 is commonly used in PDT. Ce6 can be photo-activated by near-infrared light (NIR) and eliminated from the body relatively quickly, and has high reactive oxygen generation efficiency; moreover, Ce6 can also be used for NIR fluorescence imaging, with a wavelength range of 650-900 nm, so as to avoid the in-vivo interference of endogenous chromophores. However, Ce6 has poor stability, fluorescence quantum yield ($\Phi_f$) and photosensitive effect under physiological conditions. Therefore, in order to enhance the stability of photosensitizers and their targeting to tumor tissues, in addition to developing a new generation of photosensitizers, various nano carriers are developed to provide a new platform for Ce6 so as to improve the PDT efficiency, and different therapies are effectively integrated to improve the tumor therapeutic effects, which are very necessary.

SUMMARY OF THE INVENTION

Technical Problem

The purpose of the present invention is to disclose a platinum-based drug/photosensitizer-loaded protein nanoparticle, and a preparation method for, and use of. The present invention prepares HSA nanoparticles under mild reaction conditions, in particular through appropriate prescription and process, so as to achieve effective control of particle size and improve targeting and therapeutic effects on tumors. Based on the protein template, the present invention prepares protein nanoparticles with the combined chemotherapy and photodynamic therapy effects through biomimetic synthesis for research. With HSA as a protein template, a chemotherapy drug (the cisplatin precursor ion) and the photosensitizer Ce6 are made to co-precipitate in the albumin cavity, and then nucleate and grow, so as to prepare small-particle-size albumin nanoparticles with dual functions of chemotherapy and photodynamic therapy, thereby improving the delivery efficiency of the two drugs with low water solubility as well as enhancing the drug uptake capability of tumor cells and drug accumulation in cells. After the protein nanoparticles enter the lysosome of tumor cells, Ce6 generates a significant photodynamic action under the excitation of near-infrared light, and it can also induce lysosomal rupture through ROS, and promote the platinum-based drugs to be transported into cytoplasm and then into nucleuses to exist in the active form of bivalent platinum, so as to enhance the chemotherapy effect, thus achieving the combined treatment of tumors and exerting a synergistic effect. The protein nanoparticles show good tumor targeting in vivo when used in vivo, and they combine the photodynamic therapy while they make the platinum-based drugs play a role in chemotherapy to inhibit tumor growth, thus achieving the effects of completely eliminating tumors and inhibiting tumor metastasis. In particular, the nanoparticles can be effectively metabolized in the organism due to the renal clearance effect resulted from a small particle size (<10 nm), thus having good biosafety.

Technical Solution

In order to achieve the above purpose, the present invention adopts the following technical solution:

The platinum-based drug/photosensitizer-loaded protein nanoparticle comprises a platinum-based drug/photosensitizer complex, and a protein that encapsulates the platinum-based drug/photosensitizer complex, and the platinum-based drug is the diammine dihydrate platinum ion, and the photosensitizer is chlorin e6.

In the diammine dihydrate platinum ion-loaded nanoparticles of the present invention, the platinum element is quantitatively determined, and cisplatin is used as a control, with reliable results obtained; and cisplatin is used as a control in the cell and in-vivo experiments, with reliable results obtained. The prior art cannot directly prepare the diammine dihydrate platinum ion-loaded protein nanoparticles, nor can it prepare nanoparticles loaded with both cisplatin and Ce6. Through creative work, the present invention uses safe HSA to get the diammine dihydrate platinum ion and the photosensitizer Ce6 co-loaded, having advantages such as mild conditions, simple process, small and controllable particle size, as well as good biocompatibility, tumor targeting and retention; and the nanoparticles obtained by the present invention are new albumin nanoparticles that integrate chemotherapy and photodynamic therapy, thereby realizing the preparation and application of albumin nanoparticles for efficient and low-toxic treatment of tumors and inhibition of tumor metastasis.

The present invention discloses a preparation method for the platinum-based drug/photosensitizer-loaded protein nanoparticles, which comprises the following steps: adding a solution of chlorin e6 to a mixed solution of the diammine dihydrate platinum ion and protein, reacting, and then carrying out centrifugal ultrafiltration to obtain the platinum-based drug/photosensitizer-loaded protein nanoparticles. The present invention selects a protein nano carrier, and simultaneously loads it with a platinum-based drug and a photosensitizer, so as to achieve the dual targeting therapeutic effects on tumors by combining the chemotherapy toxicity and phototoxicity on a nano drug-loaded platform. The particle size of the platinum-based drug/photosensitizer-loaded protein nanoparticle is range from 2 nm to 50 nm, and the hydrated particle size is range from 20 nm to 150 nm.

In the present invention, the dosage ratio of the protein to the diammine dihydrate platinum ion to the chlorin e6 is 100 mg:(20-50 μmol):(3-15 μmol), preferably 100 mg:(25-40 μmol):(5-10 μmol); the solution of chlorin e6 is added to the mixed solution of the diammine dihydrate platinum ion and protein, the pH is adjusted to 4.0-8.0, preferably 5.0-6.5, and then reaction is carried out at 25° C.-60° C. for 1-8 h; and the speed of centrifugal ultrafiltration is range from 1500 r/min to 4000 r/min.

The protein nanoparticles prepared by using safe HSA in the present invention have ideal particle size, chemical stability, photostability and reactive oxygen generation capacity, having great application prospects in tumor treatment.

The present invention discloses the application of the above platinum-based drug/photosensitizer-loaded protein nanoparticle in the preparation of drugs, which are specifically an anti-tumor drug, further a dual anti-tumor drug of chemotherapy and photodynamic therapy.

The nanoparticles prepared by the present invention have good tumor targeting and good retention in tumors, and show strong toxicity to tumor cells, and they have a synergistic effect in combining chemotherapy and photodynamic therapy under near-infrared light, using the photodynamic therapy on injured cells and enhancing the chemotherapy effect, so as to effectively eliminate tumors and significantly inhibit tumor growth and metastasis, showing the efficient and low-toxic anti-tumor effects of chemotherapy and photodynamic therapy used in combination, thus being a safe and effective new nano formulation.

In the present invention, HSA is an endogenous substance, and will not produce toxic and inflammatory reactions; it has good stability and unique spatial structure, thus increasing the solubility of insoluble drugs; it has a good protective effect on easily oxidized drugs, and can significantly extend the half-life period of drugs, improve targeting, and significantly reduce the toxicity of drugs; besides, because the energy and nutrient source required for tumor growth depend on albumin, endogenous albumin has an aggregation effect in tumor tissues, so that HSA has significant advantages as a drug carrier for the preparation of a drug delivery system: moreover, it has high binding capacity with drugs, good stability (producing no harmful substances at pH 4-9 and 60° C. for 10 h), good biocompatibility and biodegradability, good tumor targeting, and high efficiency and low toxicity in treating tumors, so it is of great research value.

The protein nano drug delivery system designed by the present invention is loaded with the diammine dihydrate platinum ion, which forms an adduct with DNA, thereby inhibiting DNA replication and transcription, leading to DNA breakage and mismatch, thus inhibiting cell mitosis. Therefore, it is very meaningful to develop a related new formulation.

A combined treatment is an effective anti-tumor strategy that combines different anti-cancer drugs or different therapies to achieve synergistic anti-cancer effects through multiple approaches, so as to overcome and reduce drug tolerance and toxic and side effects, and improve drug efficacy. At present, the existing combined treatment strategy of platinum-based drugs is based on the combination of different chemotherapy drugs, but the combined therapeutic effects are poor in many cases; although the direct combination of existing drugs allows the dosage to be adjusted during administration, the effect is not satisfactory due to different metabolism, and sometimes the toxicity is greater. The nano drug of the present invention has less toxicity and adverse reactions, less trauma, exact therapeutic effects, and no drug tolerance. The photosensitizer (a cytotoxic agent in PDT) can absorb light of specific wavelength and convert it into useful energy, and has strong absorbance with a high extinction coefficient at a long wavelength (600-850 nm); with light having great penetrability to tissues, it has enough vitality to produce ROS, and has excellent photochemical reactivity; it has a high triplet yield and a long triplet lifetime, can effectively produce ROS, and has the minimal dark toxicity; in addition, it is only cytotoxic in the presence of light, preferentially retained by target tissues, and rapidly excreted from the body, resulting in low systemic toxicity.

Beneficial Effects of the Invention

Beneficial Effects

In the prior art, it is difficult to control the particle size of organic molecules loaded on a protein within an ideal range.

Besides, for the protein nanoparticles reported currently, $Gd_2O_3$/Ce6-loaded nanoparticles need to be prepared with, for example, bovine serum albumin (BSA) under strong alkaline conditions (such as pH 12) for integrated diagnosis and treatment research. At present, there is no report on the preparation of albumin nanoparticles loaded with both platinum-based drugs and photosensitizers. In particular, it has not yet been found in the prior art that HSA is used under near-neutral conditions to prepare protein nanoparticles loaded with two compounds for chemotherapy and photodynamic therapy, so as to achieve the effects of combined treatment of tumors and inhibition of metastasis.

BRIEF DESCRIPTION OF THE DRAWINGS

Description of the Drawings

Figure 1:
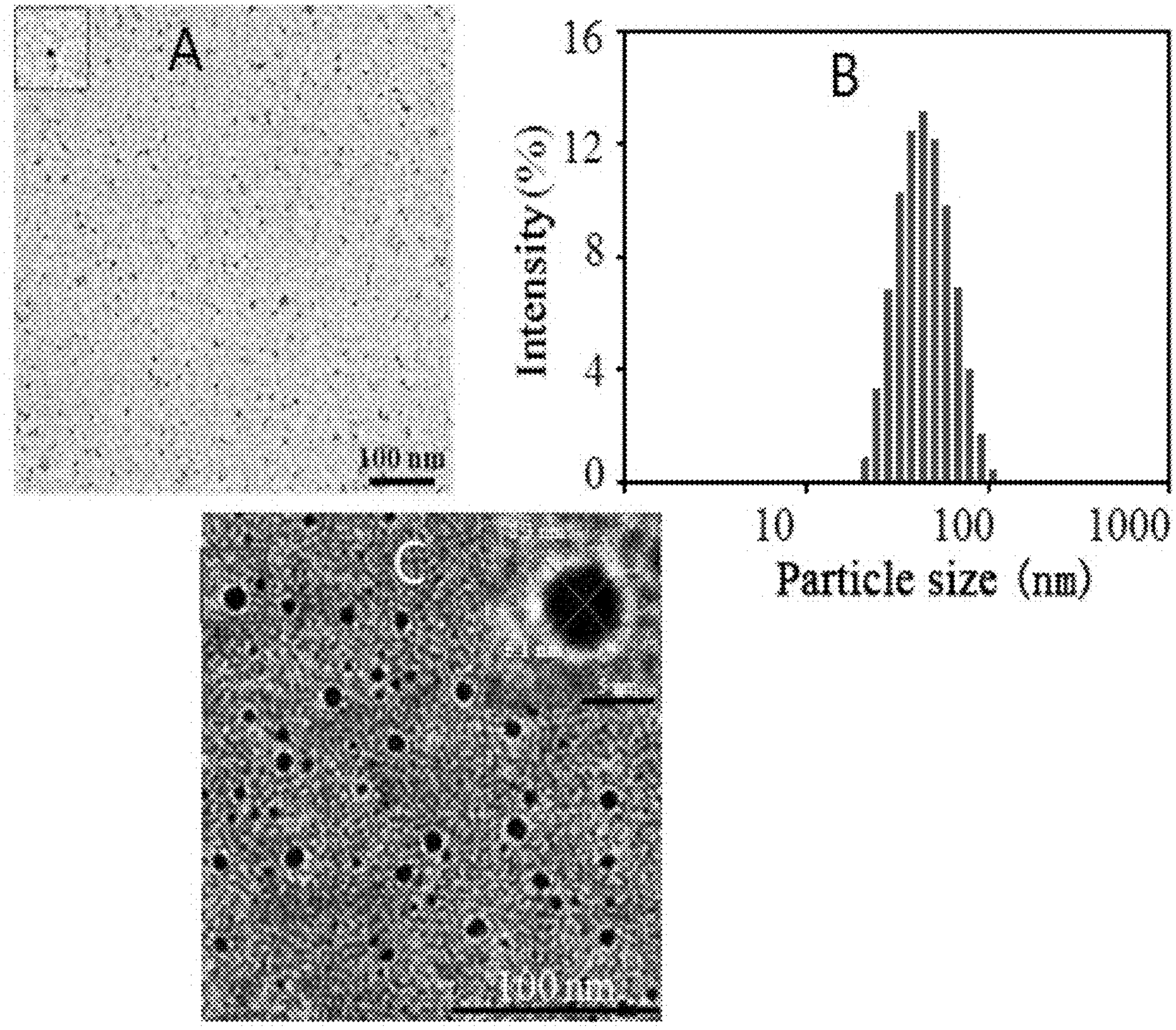

FIG. 1: Morphological characterization diagrams of the nanoparticles, in which A. transmission electron microscopy (TEM) of nanoparticles; B. dynamic particle size distribution of nanoparticles; and C. negative-staining electron microscopy of nanoparticles.

Figure 2:
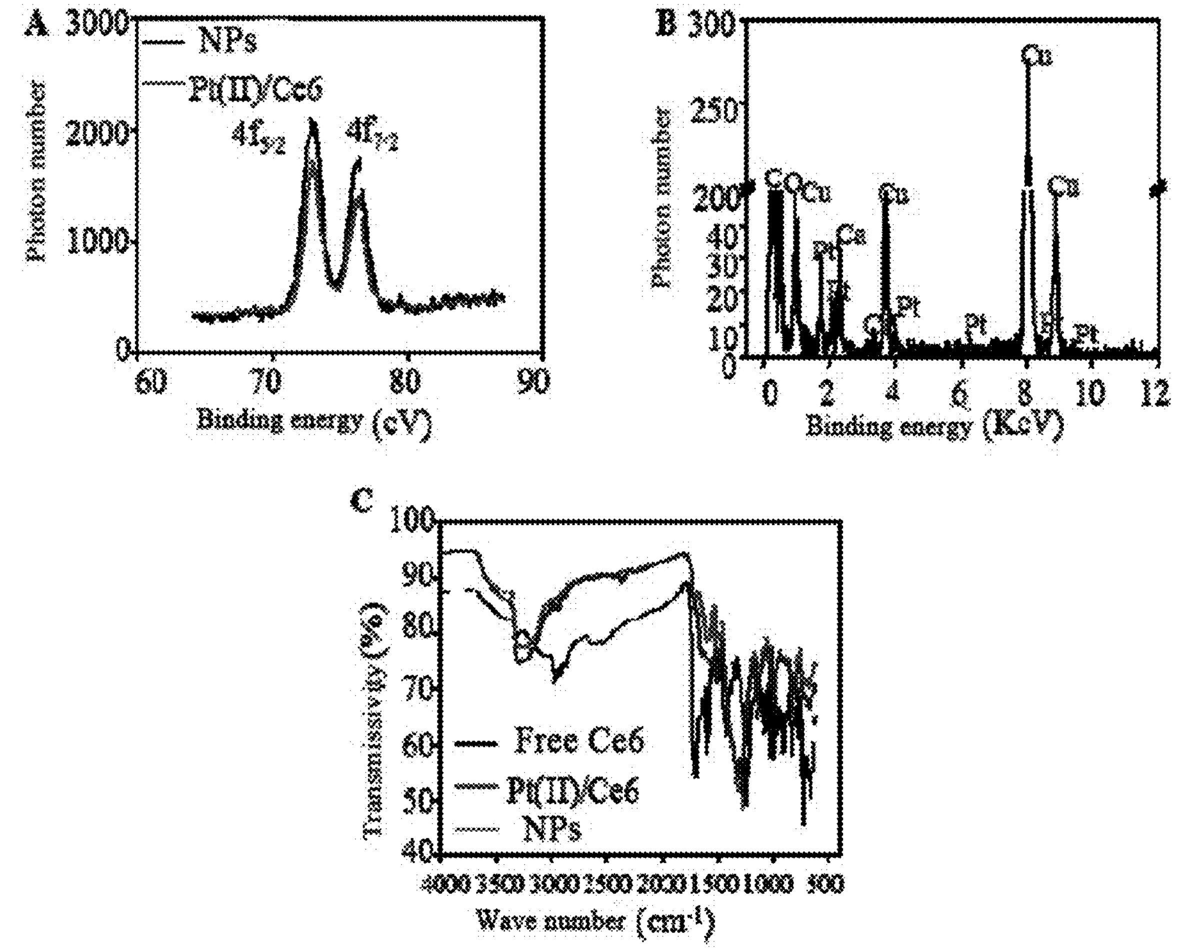

FIG. 2: Structural characterization diagrams of the nanoparticles, in which A. XPS analysis spectrum; B. EDX analysis spectrum; and C. FTIR analysis spectrum.

Figure 3:
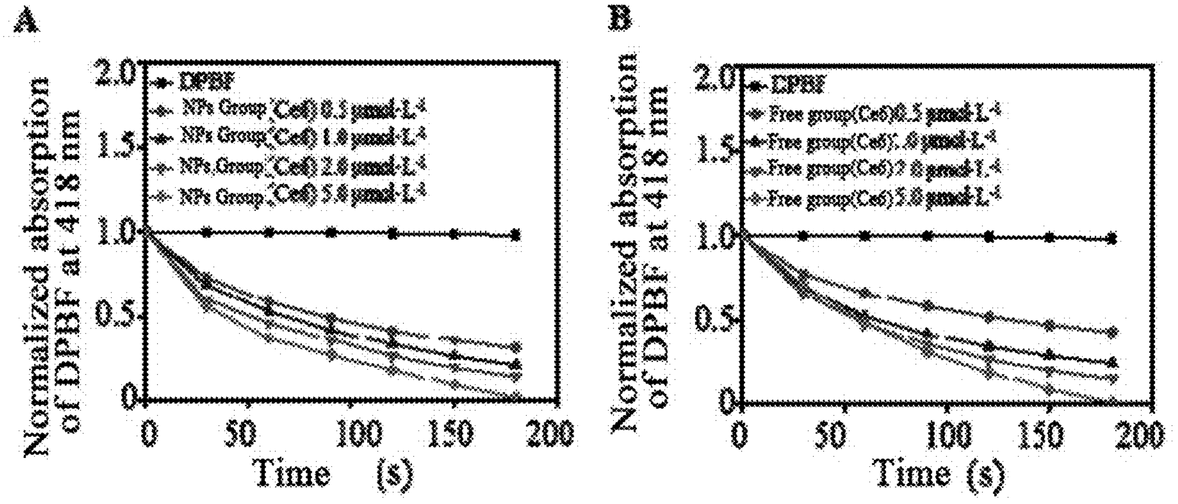

FIG. 3: Normalized absorption change diagrams of reactive oxygen generation, in which A. nanoparticles; and B. free photosensitizers.

Figure 4:
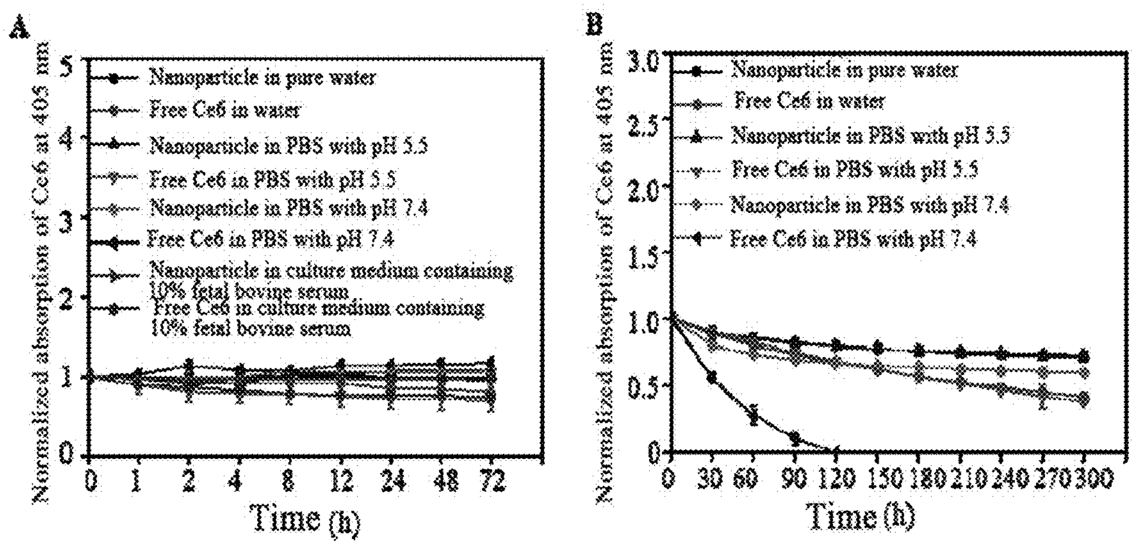

FIG. 4: Investigation results of in-vitro stability of the nanoparticles, in which A. chemical stability; and B. photostability.

Figure 5:
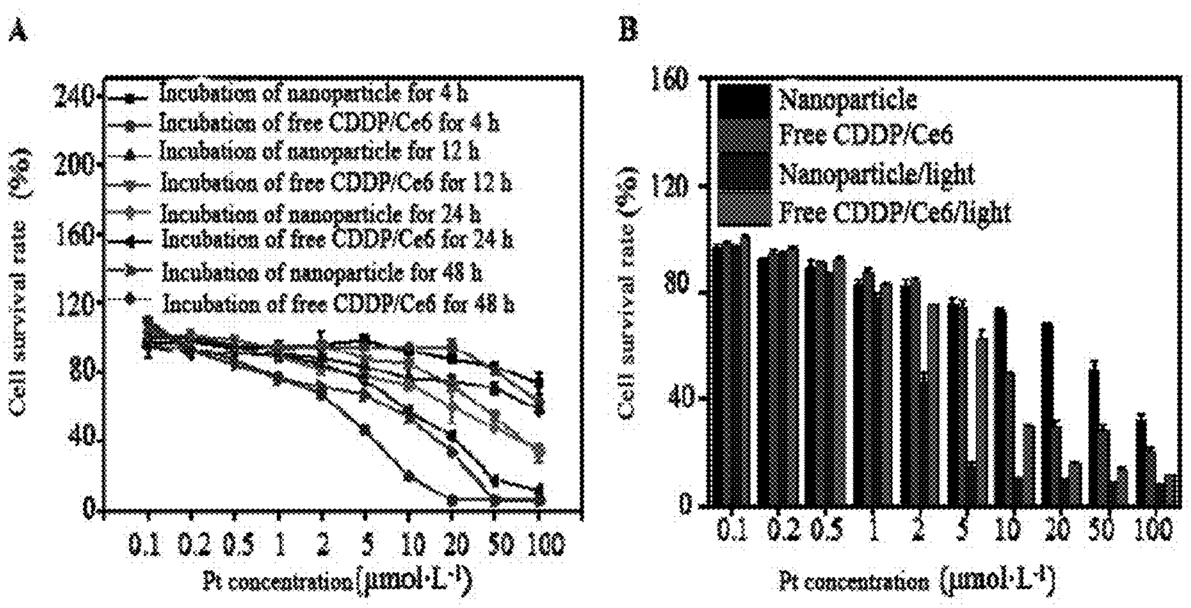

FIG. 5: Cytotoxicity of the nanoparticles on 4T1 cells.

Figure 6:
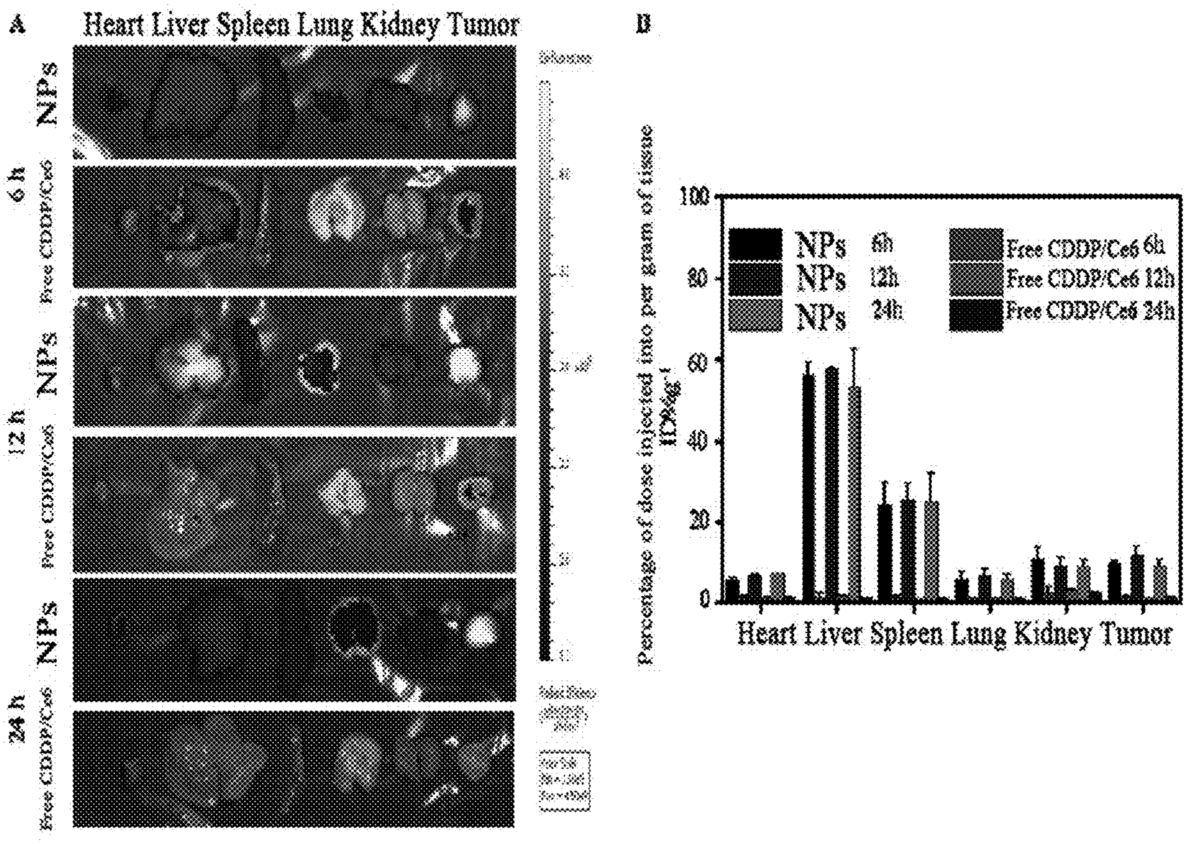

FIG. 6: Distribution of the nanoparticles in the tissues of mice.

Figure 7:
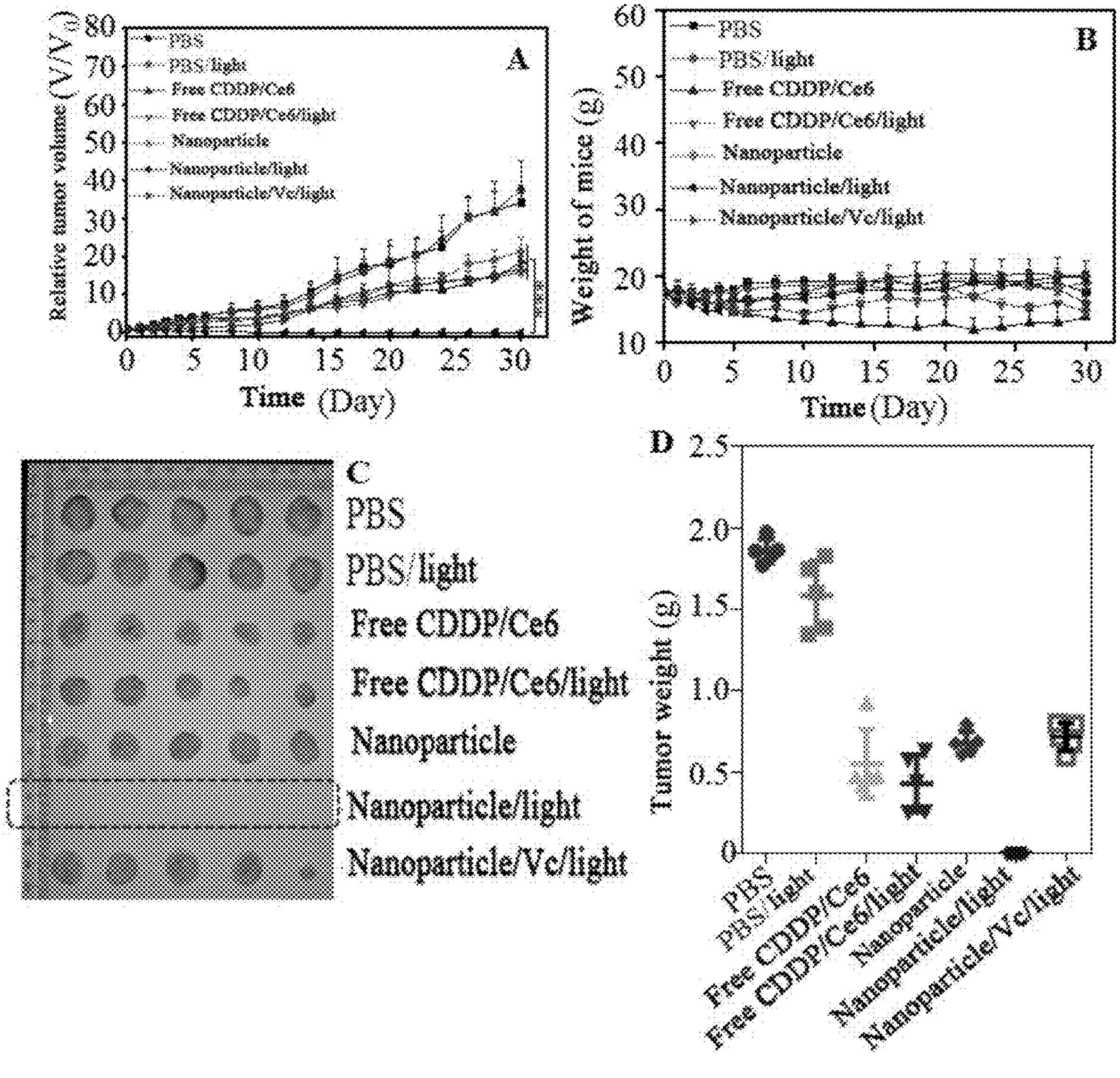

FIG. 7: Experimental results of the nanoparticles inhibiting the subcutaneous tumor in mice.

Figure 8:
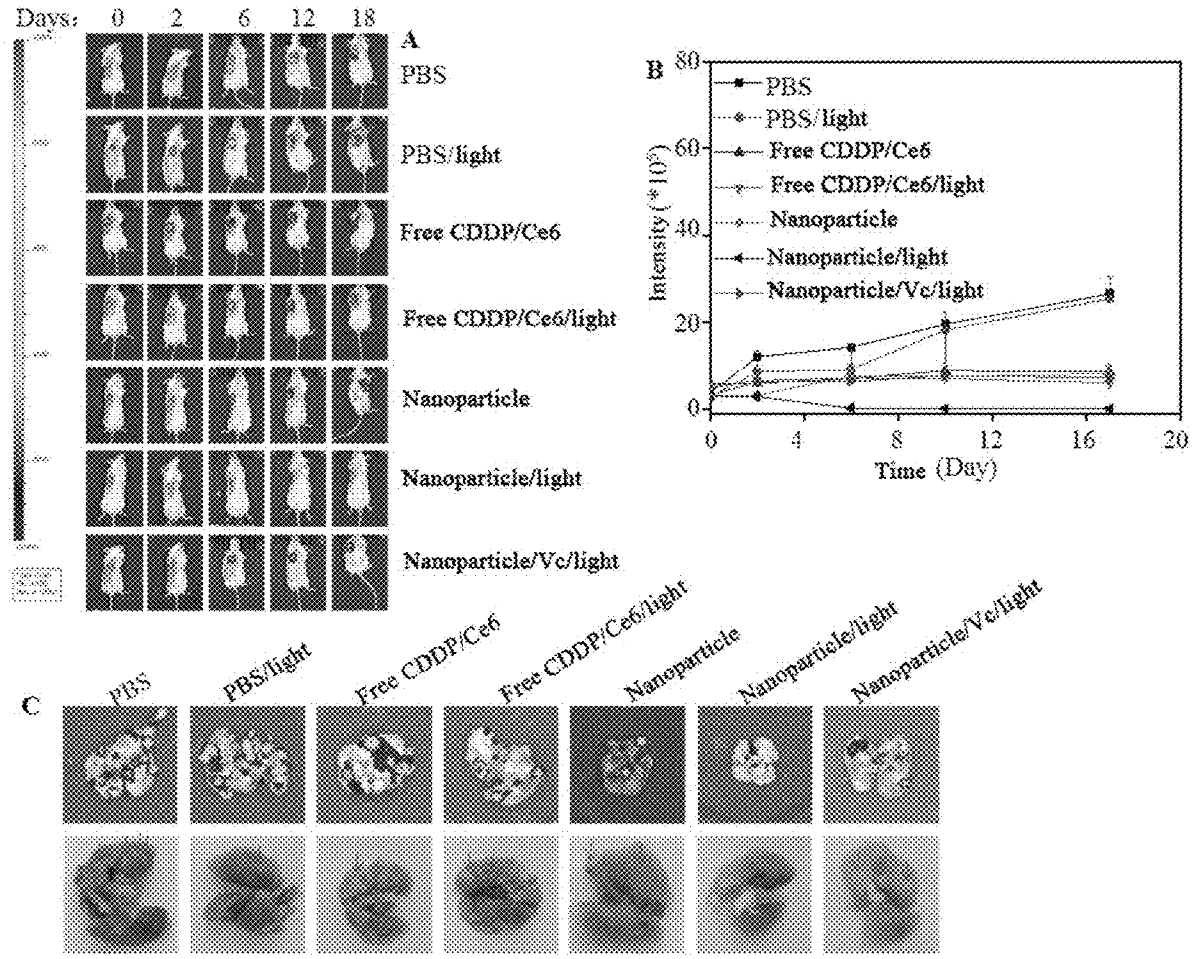

FIG. 8: Results of the nanoparticles inhibiting the lung metastatic tumor of the in-situ breast cancer in mice.

Figure 9:
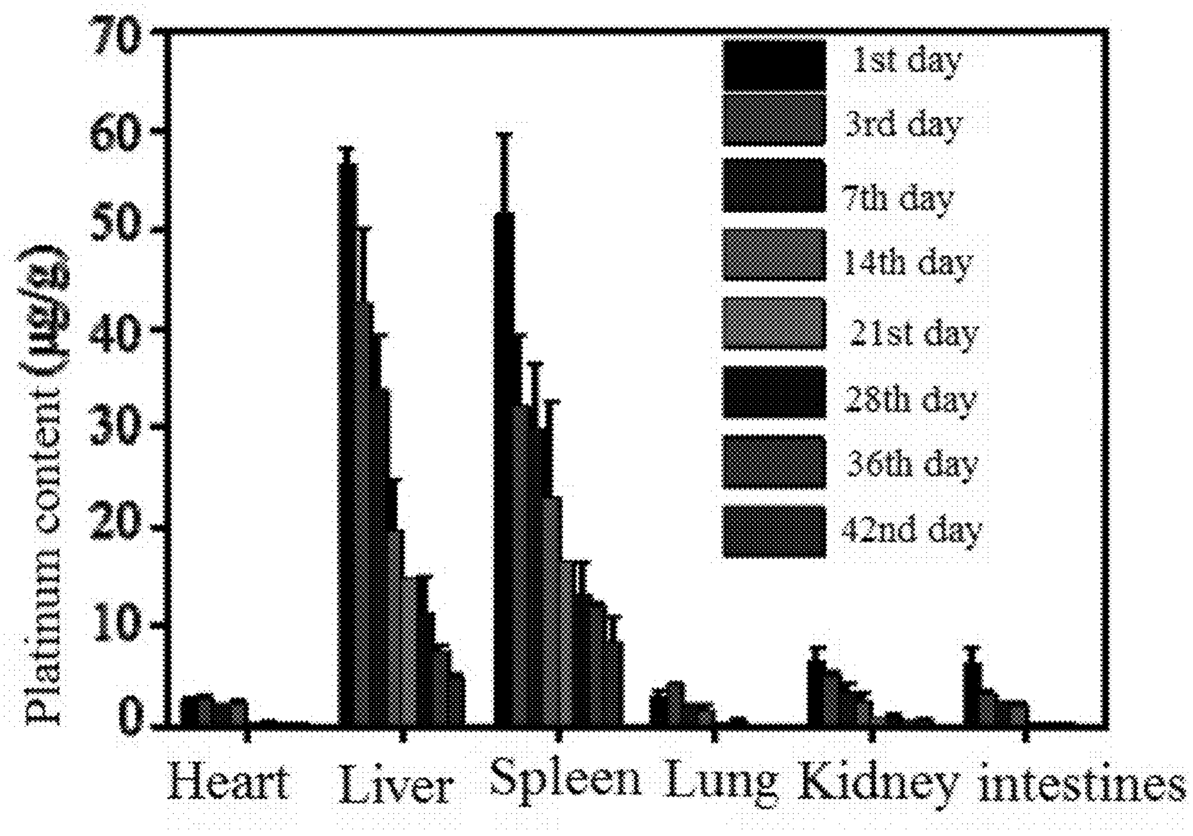

FIG. 9: Long-term distribution of the platinum element in various tissues of mice after caudal vein injection of the nanoparticles.

Figure 10:
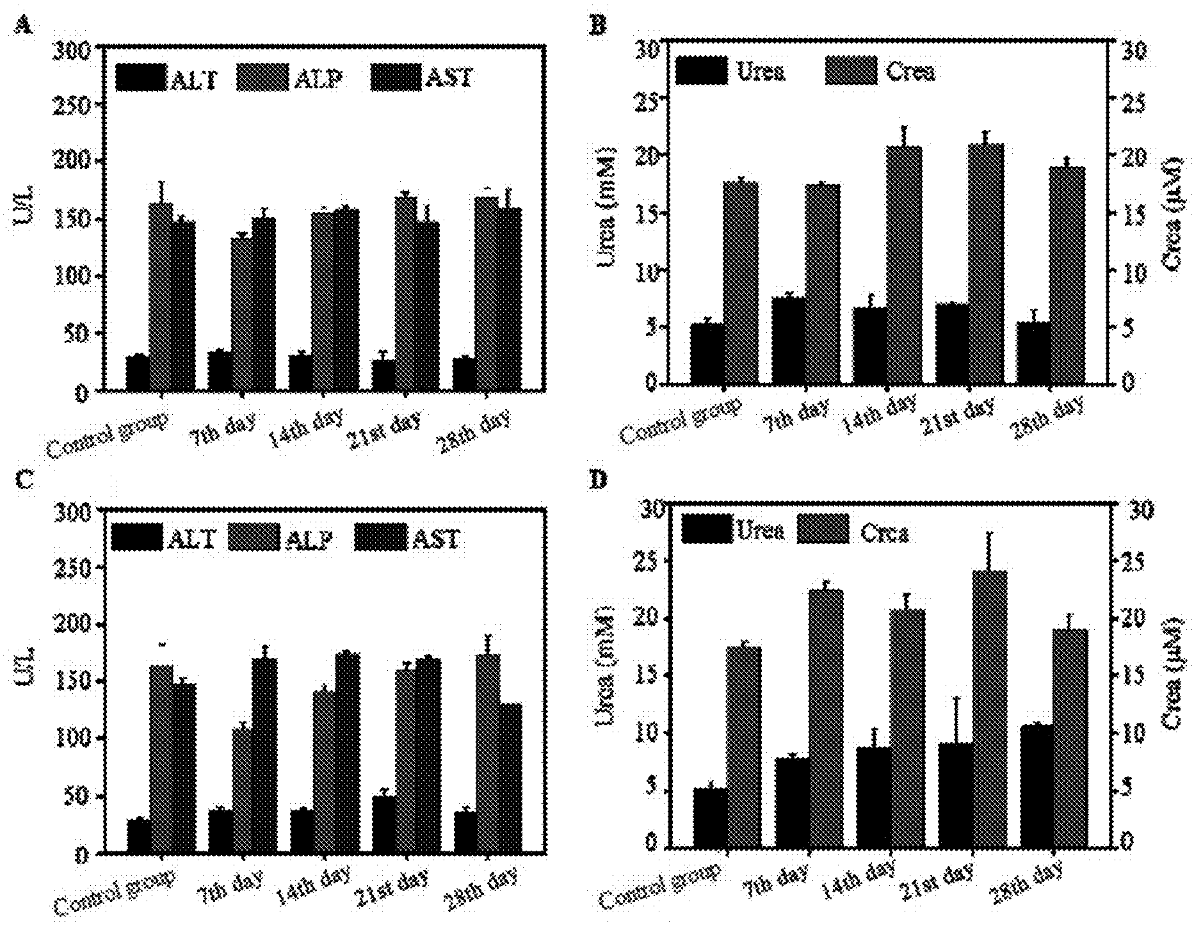

FIG. 10: Levels of ALT, AST and ALP (A) as well as Urea and Crea (B) in serum of mice at different times after the intravenous injection of nanoparticles; and levels of ALT, AST and ALP (C) as well as Urea and Crea (D) in serum of mice at different times after the intravenous injection of cisplatin.

Figure 11:
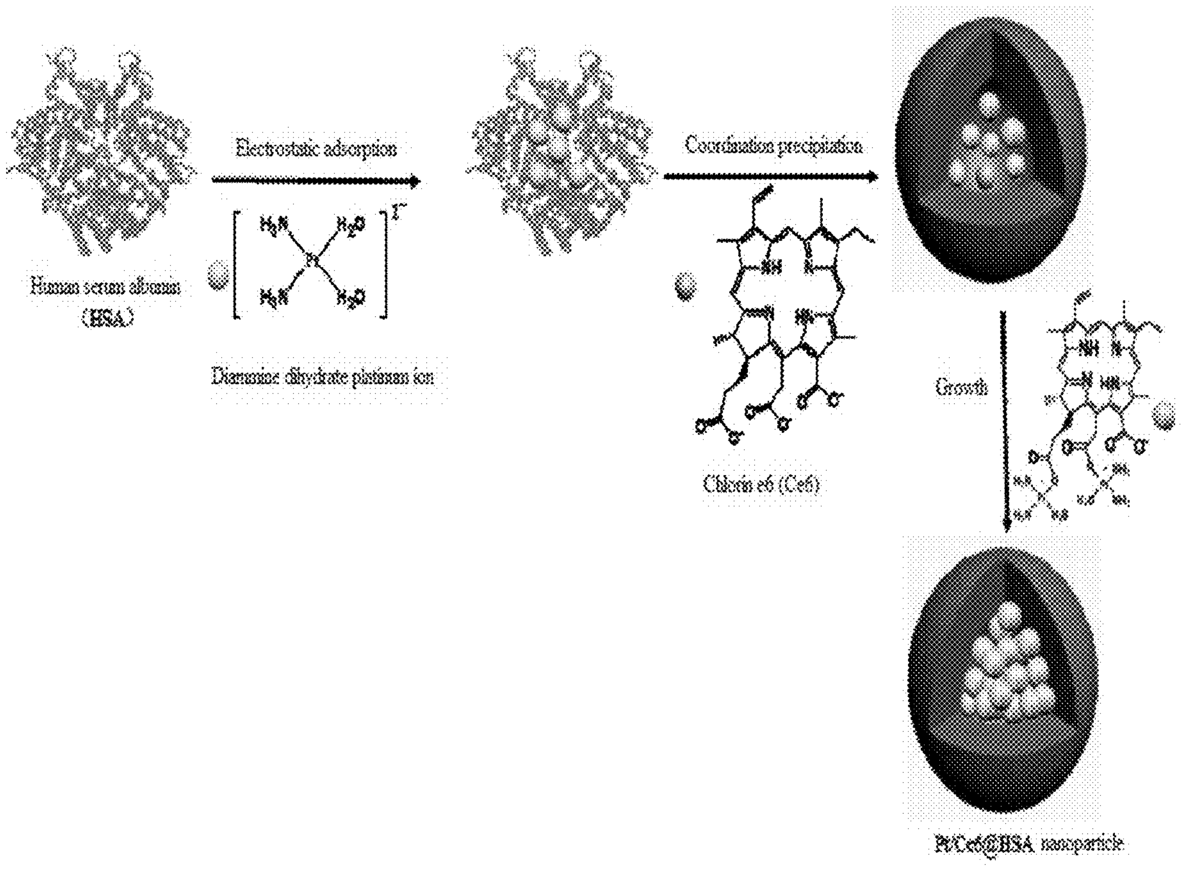

FIG. 11: Preparation process of the nanoparticles.

Figure 12:
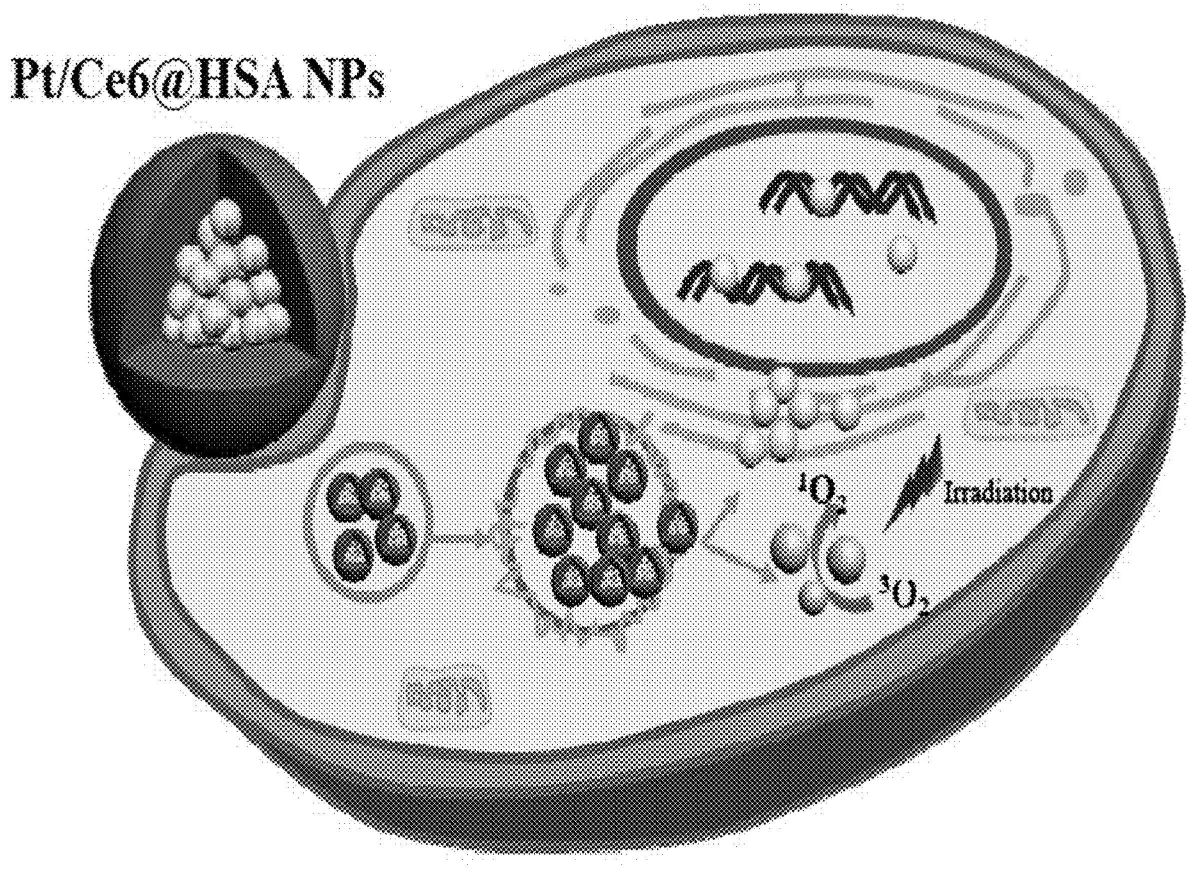

FIG. 12: Mechanism of combination chemotherapy with PDT.

DETAILED DESCRIPTION OF THE EMBODIMENTS

Embodiments of the Invention

The present invention relates to the preparation of an albumin nanoparticle with dual therapeutic effects, which is loaded with a platinum-based drug (such as the cisplatin precursor ion and the diammine dihydrate platinum ion) and a photosensitizer (such as the chlorin e6); as a new formulation of anti-tumor drugs, the nanoparticle can enhance the toxicity and targeting of drugs to tumors, exert a synergistic effect, and reduce systemic toxic and side effects, so as to achieve combined treatment of tumors and inhibit tumor metastasis.

In the present invention, a solution of chlorin e6 is added to a mixed solution of the diammine dihydrate platinum ion and protein for reaction and, after completion of the reaction, centrifugal ultrafiltration is carried out to obtain the platinum-based drug/photosensitizer-loaded protein nanoparticles. The steps are specifically as follows:

(1) making cisplatin react with a silver nitrate solution to obtain an aqueous solution of diammine dihydrate platinum nitrate, and then mixing the diammine dihydrate platinum nitrate solution with a protein solution, with the concentration of the diammine dihydrate platinum nitrate solution at 8-32 mmol/L and the concentration of the protein solution at 5-20 mg/mL;

(2) adding a Ce6 solution to the mixed solution in step (1), adjusting the pH to 4.0-8.0, with the concentration of the Ce6 solution at 2-8 mmol/L, and then making the mixed solution react at 25° C.-60° C. for 1-8 h;

(3) putting the mixture obtained from the reaction in step (1) into an ultrafiltration centrifugal tube, and removing free small molecules by centrifugal ultrafiltration at a speed of 1500-4000 r/min until the lower-layer filtrate is colorless; and in the present invention, making the diammine dihydrate platinum ion react with Ce6 to form a complex, and co-precipitating in a protein cavity to obtain the nanoparticles.

In the present invention, the chemical structural formula of the platinum-based drug/photosensitizer complex is as follows:

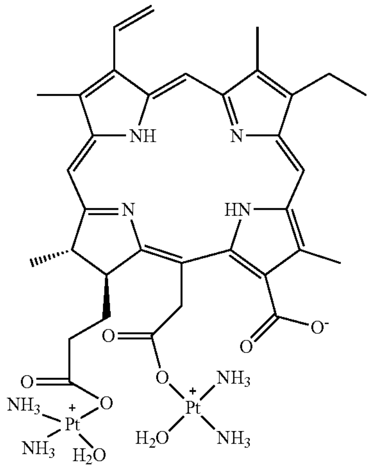

The outer-shell electrons of a platinum atom are 4f14 5d10 6s1, those of a divalent platinum ion are 4f14 5d9, and those of a divalent platinum ion are 4f14 5d7; and the reaction of the outer-shell electrons 4f14 5d9 of the divalent platinum ion with one —$COO^-$ produces a monovalent platinum ion, whose outer-shell electrons are 4f14 5d10. The reaction of the photosensitizer with the diammine dihydrate platinum ion is shown below.

Ce6 Diammine Dihydrate Platinum Nitrate Complex $$R_1—COO^-+H^++R_2^+—H_2O+NO_3^-=R_1—COO—R_2^++H^++NO_3^-+H_2O$$

$$R_1\text{-}2COO^-+2H^++2R_2^+—H_2O+2NO_3^-=R_1\text{-}2COO\text{-}2R_2^+2H^++2NO_3^-+2H_2O$$

$$R_1\text{-}3COO^-+3H^++3R_2^+—H_2O+3NO_3^-=R_1\text{-}3COO\text{-}3R_2^++3H^++3NO_3^-+3H_2O$$

The specific embodiments of the present invention will be further described in detail below in combination with the drawings and examples. The following examples are used to explain the present invention, but the present invention is not limited thereto. The platinum-based drug/photosensitizer-loaded protein nanoparticles of the present invention are referred to as "nanoparticles" for short.

Example 1: weighing 720 mg of cisplatin ($Pt(NH_3)_2Cl_2$, 2.4 mmol/L) and 800 mg of silver nitrate ($AgNO_3$, 4.7 mmol/L), dissolving them in 6.0 mL of distilled water, stirring in a water bath at 60° C. for 3 h in dark, and then stirring at room temperature for 20 h; after completion of the reaction, taking out the reaction liquid (clear without turbidity), centrifugating the liquid at a speed of 14000 r/min for 15 min to remove the generated AgCl precipitation, and filtering the supernatant with a 0.22 μm filter membrane to obtain a solution of diammine dihydrate platinum nitrate ($[Pt(NH_3)_2(H_2O)_2](NO_3)_2$); determining the concentration of the solution with an inductively coupled plasma optical emission spectrometer (ICP-OES), adding water to the solution to adjust the final concentration thereof to 320 mmol/L for storage, and diluting the stored solution with water to a concentration of 32 mmol/L when preparing the nanoparticles;

adding 1 mL of a diammine dihydrate platinum precursor ion solution with a concentration of 32 mmol/L to 10 mL of an HAS aqueous solution with a concentration of 10 mg/mL, adding 1 mL of a Ce6 solution with a concentration of 8 mmol/L while stirring, adjusting the system to pH 5.5 with a sodium hydroxide aqueous solution (0.1 M), and then stirring in a water bath at 55° C. for 4 h; after completion of the reaction, centrifuging the reaction liquid (3000 r/min, 10 min), and purifying by ultrafiltration (MW: 100 kD, 2000 r/min, 10 min) to remove the free diammine dihydrate platinum precursor ion and Ce6; finally, filtering the purified reaction liquid with a filter membrane having a pore diameter of 0.22 μm, thus obtaining a solution of albumin nanoparticles (Pt/Ce6@HSA NPs) loaded with a platinum drug (diammine dihydrate platinum)/a photosensitizer (Ce6), referred to as a nanoparticle solution.

Morphological characterization of nanoparticles: (1) Transmission electron microscopy characterization of nanoparticles: dropping 20 μL of the nanoparticle solution onto a copper-mesh carbon film, putting the film into a dryer to evaporate the water, and then observing the morphology with a 120 kV transmission electron microscope (TEM). The results were shown in FIG. 1-A. It could be seen that the prepared nanoparticles were regularly round with a particle size of 4.9±1.0 nm.

In the presence of heavy metals, only the heavy metals in the core of nanoparticles were shown by TEM, and albumin was not imaged; through a protein staining experiment, it was found by TEM measurement that the particle size of nanoparticles inclusive of a protein layer was 7.9±0.4 nm.

(2) Characterization of particle size and distribution of nanoparticles: 1 mL of the nanoparticle solution was taken, and analyzed for the particle size and distribution with a laser scattering particle size analyzer. The results were shown in FIG. 1-B. It could be seen that the protein nanoparticles prepared had a single-peak distribution, with an average hydrated particle size of 33.1 nm (including a hydrated layer on the surface) and a polydispersity index (PDI) of 0.198, which was conducive to avoiding the interception of endothelial reticular cells, forming a long blood circulation, and playing a passive targeting role.

(3) Negative-staining electron microscopy of nanoparticles: dropping the nanoparticle solution onto a copper mesh, 5 min later soaking up the excess liquid, dropping a 0.2% uranium acetate aqueous solution to dye for 3 min, then soaking up the dye solution with filter paper, drying, and then observing with a 120 kV electron microscope. The results were shown in FIG. 1-C. After the negative staining, it could be seen that the protein of the nanoparticle was distributed in the outer layer of the nanoparticle and was light white, with the background around and inside the nanoparticle being dark; after the nanoparticle was locally magnified, it was found that the particle size of the outer protein layer was about 8 nm, the particle size of the core was 5 nm, and the size of the single-molecule cavity was generally 6-8 nm, which indicated that a complex of the diammine dihydrate platinum ion and Ce6 existed in the core of the nanoparticle prepared by the present invention.

The above results showed that the nanoparticles prepared by the present invention were regularly round, with uniform dispersion and a particle size less than 10 nm; and they could be cleared by the kidney, and had the EPR effect in vivo and the tumor targeting effect.

Preparation of free CDDP/Ce6 solution: dissolving cisplatin and Ce6 respectively with normal saline and DMSO, mixing according to a molar ratio of Pt:Ce6=1.5:1, and diluting with water to the required concentration, thus obtaining the free CDDP/Ce6 solution.

Structural characterization of nanoparticles: (1) Binding energy of inner-shell electrons of Pt ligands of nanoparticles: pre-freezing a prepared solution of nanoparticles in a refrigerator at −80° C., then placing the nanoparticles in a vacuum frozen dryer to freeze-dry for 48 h, then grinding them into fine powder in a mortar, and then analyzing the atomic valence of the nanoparticles and free physical mixture with the X-ray photoelectron spectroscopy (XPS). The results were shown in FIG. 2-A. According to the peak fitting process of the $4_f$ orbital of Pt element in the X-ray photoelectron spectrum (XPS) thereof, it was found that the peaks of the nanoparticles appeared at 72.9 and 76.4 eV, which indicated that there was divalent platinum in the nanoparticles, consistent with the results of the control group of the free diammine dihydrate platinum ion/Ce6 mixture.

(2) Element analysis of nanoparticles: dropping a solution of nanoparticles onto an ultra-thin carbon film, evaporating the water, and then conducting the energy dispersive X-ray (EDX) analysis to determine the element composition of nanoparticles. The results were shown in FIG. 2-B. It could be seen that platinum existed in the nanoparticles.

(3) Coordination analysis of nanoparticles: The freeze-dried nanoparticle powder, free diammine dihydrate platinum ion/Ce6 mixture and Ce6 powder were analyzed by the Fourier transform infrared (FTIR) spectroscopy. The results were shown in FIG. 2-C.

Singlet oxygen generation capacity of nanoparticles: Changes in absorbance before and after capture of the singlet oxygen were measured with 1,3-diphenylisobenzofuran (DPBF). The steps were as follows: diluting the prepared nanoparticle solution and free Ce6 solution into samples respectively with a Ce6 concentration of 0.5, 1.0, 2.0 and 5.0 μmol/L, taking 2.97 mL respectively into a quartz cuvette, and measuring the initial UV absorption value; using DMSO to prepare a 30 μmol/L DPBF solution, and taking 30 μL into the quartz cuvette; and irradiating the solution with a 660 nm laser (0.15 $W/cm^2$) for 3 min while stirring, during which measuring the change of the UV absorption value of DPBF at 418 nm every 30 s, and making a normalized broken-line graph thereof. The results were shown in FIG. 3. Figs. A and B were a normalized diagram of the absorbance value of DPBF respectively in the nanoparticle solution and the free Ce6 solution as a function of irradiation time. It could be seen from Fig. A that the absorbance of DPBF decreased rapidly with the irradiation time when the concentration of the nanoparticle solution was low, and the absorbance was concentration dependent, which indicated that there was a large amount of singlet oxygen generated, and the nanoparticles had strong singlet oxygen generation capacity and thus had potential in the application of PDT; however, it could be seen from Fig. B that the free Ce6, with the same concentration, only generated a small amount of singlet oxygen.

In-vitro stability of nanoparticles: (1) Chemical stability of nanoparticles: taking 0.1 mL of a nanoparticle solution with the concentration of Ce6 at 20 μmol/L and 0.1 mL of a free Ce6 solution with a concentration of 20 μmol/L, respectively, and adding them respectively to 2.9 mL of pure water, a phosphate buffer with pH 5.5, a phosphate buffer with pH 7.4, and a RPMI 1640 culture medium containing 10% fetal bovine serum; and storing at room temperature and away from light, with 3 copies for each environment. A UV-vis spectrophotometer was used to measure the absorbance change of Ce6 within 72 h. The results were shown in FIG. 4A. It could be seen that the UV absorption values of nanoparticles in the deionized water, the phosphate buffer with pH 5.5, the phosphate buffer with pH 7.4, and the culture medium containing 10% fetal bovine serum were basically unchanged within 72 h, indicating that the nanoparticles had better stability, which was helpful to the play of drug efficacy of the nanoparticles; however, the UV absorption of the free Ce6 group decreased by 20%-40% with time.

(2) Photostability of nanoparticles: taking 0.1 mL of a nanoparticle solution with the concentration of Ce6 at 20 μmol/L and 0.1 mL of a free Ce6 solution with a concentration of 20 μmol/L, respectively, and adding them respectively to 2.9 mL of pure water, a phosphate buffer with pH 5.5, and a phosphate buffer with pH 7.4; and using a 660 nm laser with the power of 0.15 $W/cm^2$ to irradiate the solutions once every 30 s, and immediately measuring the ultraviolet absorption value with a UV-vis spectrophotometer until full 5 min of irradiation. The results were shown in FIG. 4B. It could be seen that after being encapsulated in a protein, Ce6 formed a complex with platinum, which had a certain stabilizing effect on Ce6, so that the nanoparticle had better photostability in deionized water and acidic and neutral environments; however, the free Ce6 could be photobleached quickly under irradiation, especially in an acidic environment where photobleaching was completed within 120 s, having low solubility and poor stability.

Therefore, the loading nanoparticles would help to improve the stability and play the role of PDT in the acidic environment of tumors.

Cytotoxicity of nanoparticles: taking a single-cell suspension of 4T1 mouse breast cancer cells in the logarithmic phase, and inoculating it into a 96-well cell culture plate ($1.0\times10^5$ cells/well, a 1640 culture medium) at 100 μL/well; and culturing the cells in a constant-temperature cell incubator at 37° C. overnight to make them completely adhere to the wall and deform, and after the cells grew to 80%, removing the original culture medium;

dividing the samples into a free drug group and a nanoparticle group, and further into a no-irradiation group and an irradiation group; and respectively adding 100 μL of the diluted nanoparticle solution and free CDDP/Ce6 solution with the same concentration to replace the original culture medium, with the concentration respectively set at 0.1, 0.2, 0.5, 1.0, 2.0, 5.0, 10.0, 20.0, 50.0, 100.0 μmol/L (calculated according to the concentration of Pt element) and 4 wells in copies for each concentration;

for investigating the chemotherapy cytotoxicity of nanoparticles, culturing the no-irradiation group respectively for 4, 12, 24 and 48 h, then discarding the culture medium with the drug, and then adding 10 μL of a 5 mg/mL MTT solution and 90 μL of a 1640 culture medium to each well; continuing the cultivation for 4 h, then discarding the liquid, and then adding 150 μL of DMSO to each well; using a microplate reader to set a concussion of 30 s, and with the ultraviolet absorption at 490 nm, measuring the absorbance A; and taking the average value of the wells in copies to calculate the cell survival rate as follows: cell survival rate=experimental group A/negative control group $A_0\times100\%$ (taking the cells without the drug as the negative control group). The results were shown in FIG. 5*a*.

In order to explore the therapeutic effects of chemotherapy and photodynamic therapy used in combination, the time point at the 24th h of incubation was selected for irradiation, with the steps as follows: for the irradiation group, adding the drug, culturing for 24 h, then irradiating each well with a laser (660 nm, 0.15 $W/cm^2$, 5 min), then continuing the cultivation for 24 h, and then continuing the same operation processes such as adding MTT. The results were shown in FIG. 5*b*.

As shown in FIG. 5, when only the chemotherapy effect existed, the drug in the nanoparticles was slowly released in cells, which resulted in long-term cytotoxicity, indicating that the drug had the potential of high efficiency and low toxicity; under irradiation conditions, compared with the free drug group, the cell survival rate of the nanoparticle group decreased significantly when calculated according to the concentration of Pt element, $IC_{50}$ decreased from 40.91 μmol/L to 1.91 μmol/L under no-irradiation conditions, with a reduction of 21.5 times, while the free group had a dark $IC_{50}$ of 9.52 μmol/L and a light $IC_{50}$ of 6.18 μmol/L, with a reduction of only 1.5 times. These results showed that the photodynamic effect of the drug played a significant role in killing tumor cells, reflecting the advantages of the present invention combining chemotherapy with photodynamic therapy.

The nanoparticles prepared in Example 1 of the patent CN110368374A were taken for the same cytotoxicity test as above. The no-irradiation $IC_{50}$, calculated according to the concentration of Pt element, was 87.86 μmol/L.

Distribution of nanoparticles in tissues of mice: (1) Establishment of subcutaneous tumor model: culturing 4T1 tumor cells, collecting the tumor cells in the logarithmic phase, and then digesting and centrifuging them; adding a serum-free culture medium to wash once, centrifugating, then adding a pre-cooled PBS to prepare a cell suspension with a concentration of $1\times10^7$ cells/mL, and then putting the suspension in an ice box for standby; and depilating the right hind leg of the white mouse, lifting the skin from the muscle with a syringe, and then injecting 50 μL of the cell suspension. The experiment could be conducted when the tumor grew to a volume about 60-100 $mm^3$. (Tumor volume=length$\times$width$^2\div2$).

(2) Experiment of distribution in tissues: taking 18 mice bearing tumor subcutaneously and dividing them into 2 groups, and respectively injecting them with 200 μL of a nanoparticle solution and 200 μL of a free CDDP/Ce6 solution via the caudal vein at an injection dose of 5 mg/kg (calculated according to the concentration of Pt element); in 6, 12 and 24 h after the injection, taking 3 mice out from each group for cardiac perfusion with normal saline, then putting them to death through cervical dislocation, and then anatomically removing the heart, liver, spleen, lung, kidney and tumor; and observing the extracted tissues by a small-animal imaging system for the fluorescence distribution of Ce6 at each time point. The results were shown in FIG. 6A.

The subsequent steps were as follows: weighing and cutting the tissues, putting them respectively into 100 ml conical flasks, and marking the flasks; and adding aqua regia for high-temperature nitrolysis, and after complete nitrolysis of the tissues, taking 100 μL out to dilute to a certain volume, and then after membrane filtration, quantifying the platinum element in each tissue by ICP-MS. The results were shown in FIG. 6B.

As shown in FIG. 6, at different times after the intravenous injection, the nanoparticles were accumulated in tumor tissues significantly more greatly than the free drugs, and had good tumor targeting, so they had the potential to treat tumors.

Anti-tumor effects of nanoparticles on subcutaneous tumors in mice: establishing a subcutaneous tumor-bearing model of mice with the above method, and when the tumor volume reached 60 $mm^3$, administering the drug according to the following design: randomly dividing the subcutaneous tumor-bearing mice into a PBS group, a PBS-irradiation (PBS/light) group, a free CDDP/Ce6 group, a free CDDP/Ce6/light group, a nanoparticle group, a nanoparticle/light group, and a Vc-preinjected nanoparticle/light (nanoparticle/Vc/light) group; administering the drug to the mice via the caudal vein respectively on the 0th, 2nd and 5th day at an injection dose of 5 mg/kg (calculated according to the concentration of Pt element); irradiating (660 nm, 0.15 $W/cm^2$) the irradiation group for 5 min at the 12th h after each administration each time, and intratumorally injecting the nanoparticle/Vc/light group with a Vc solution (25.0 μmol/kg) half an hour before irradiation each time; measuring and recording the weight and tumor volume of mice during the 30-day tumor inhibition period; and at the end of the experiment, killing the mice, collecting the tumors, and then fixing them with 4% formaldehyde for photographing. The results were shown in FIG. 7.

As could be seen from the results of A, C and D in FIG. 7, the tumor growth in the PBS group before and after irradiation had little difference, with the tumor volume about 37 times larger than the initial volume, indicating that irradiation itself did not inhibit tumor growth; the free CDDP/Ce6 group had only chemotherapy effects under no irradiation, but it should have chemotherapy and photodynamic therapy effects after irradiation, with the tumor inhibition effect similar to that under no irradiation; the nanoparticle group, having greatly different tumor inhibition effects before and after irradiation, not only completely inhibited tumor growth but also achieved the tumor ablation effect after 3 times of administration and irradiation, which confirmed the excellent advantages of the loading nanoparticles of the present invention for combined chemotherapy and photodynamic therapy; in addition, the tumor inhibition effect was reduced after the intratumoral injection of the reductant Vc that scavenged reactive oxygen species, which confirmed the synergistic contribution of platinum-based drugs and Ce6 in the combined chemotherapy and photodynamic therapy.

As could be seen from the results of B and D in FIG. 7, due to the high toxicity of chemotherapy drugs, the weight of mice decreased by about 8 g compared with the initial weight, which severely affected the survival and health of mice, and the addition of free drugs to the photodynamic therapy could not completely eliminate tumors; and the nanoparticle/light group could not only completely eliminate the tumor, but also have little effect on the weight of mice, indicating good therapeutic effects and low toxicity. To sum up, the nanoparticles had high efficiency and low toxicity in tumor treatment.

Effects of nanoparticles inhibiting lung metastatic tumor of in-situ breast cancer in mice: (1) Model establishment of lung metastatic tumor of in-situ breast cancer: culturing 4T1-Luciferasee tumor cells, collecting the tumor cells in the logarithmic phase, digesting them to prepare a serum-free pre-cooled PBS cell suspension with a concentration of $1\times10^7$ cells/mL, and putting the suspension in an ice box for standby; and injecting 50 μL of the cell suspension into the breast pad of mice, and after inoculation, detecting the fluorescence signal intensity by a small-animal imaging system in vivo.

(2) Effect of inhibiting lung metastasis of tumor: when the fluorescence signal of the tumor site was about $3\times10^5$ $p/s/cm^2/sr$, dividing the mice bearing the tumor in situ into groups according to the above subcutaneous tumor inhibition experiment, administering drugs, and irradiating; on the 0th, 2nd, 6th, 12th and 18th day after the administration, performing bioluminescence imaging with the small-animal imaging system in vivo to detect the signal intensity of the tumor site, and before the detection, intraperitoneally injecting each mouse with a chloral hydrate anesthetic (at a dose of 35 mg/kg) and a fluorescein sodium salt (at a dose of 150 mg/kg); 10 min later, imaging by scanning to observe the growth of tumors, quantitatively analyzing the fluorescence value at each time point, and drawing a tumor growth curve; and on the last day, after completion of the scanning, dissecting the lung tissue of mice for bioluminescence imaging, and taking white-light photos. The results were shown in FIG. 8.

As shown in FIG. 8, for the PBS-treated mice, the tumors grew faster, the fluorescence signal of the tumor site was the strongest, and the lung had the most metastatic lesions; the free-drug no-irradiation group, the irradiation group and the nanoparticle no-irradiation group had limited anti-tumor effect and inhibitory effect on lung metastasis of tumors, and had a weaker fluorescence signal than the PBS group, indicating that only chemotherapy could not completely inhibit tumor growth and metastasis, and the free chemotherapy drug/photosensitizer+irradiation also had limited effects; in the nanoparticle/light group, after 3 times of treatment, the tumor could be eliminated and the metastasis of tumor to the lung could be effectively inhibited, which proved that the nanoparticles of the present invention had significant advantages in inhibiting tumor growth and tumor metastasis after combining chemotherapy and PDT; to be the same as the results of subcutaneous tumor experiment, Vc could reduce the anti-tumor effect of nanoparticles.

Long-term distribution of nanoparticles in tissues: randomly dividing the healthy Balb/c mice into 8 groups, with 3 mice in each group, and injecting them with the nanoparticle solution via the caudal vein at an injection dose of 5 mg/kg (calculated according to the concentration of Pt element); and on the 1st, 3rd, 7th, 14th, 21st, 28th and 42nd day after administration, killing the mice to dissect the heart, liver, spleen, lung, kidney and intestine, weighing each of these organs, then adding aqua regia and perchloric acid for high-temperature nitrolysis, then making the volume constant, and then detecting the content of Pt element in each organ by ICP-MS. The results were shown in FIG. 9. It could be seen from FIG. 9 that the nanoparticles were mainly distributed in the liver and spleen after injection, and the platinum content had decreased by about 90% by the 42nd day; however, the distribution of platinum in the heart, lung, kidney and intestine decreased gradually, and by the 35th day, the content of Pt element in each organ was low or even zero, indicating that the nanoparticles could be gradually removed from the tissues without heavy metal accumulation in vivo, so as to avoid long-term toxic and side effects, thus having good biosafety.

Inspection of biochemical indexes after action of nanoparticles: In order to determine the toxicity of drugs during metabolism in vivo, biochemical indexes of liver and kidney functions were investigated. The steps were as follows: detecting liver indexes including alanine aminotransferase (ALT), aspartate aminotransferase (AST) and alkaline phosphatase (ALP), as well as kidney indexes including urea and creatinine (Crea), and comparing them with the normal values to determine the injury of drugs to the liver and kidney functions;

randomly dividing healthy Balb/c mice into 3 groups, i.e. a PBS group, a Pt/Ce6@HSA nanoparticle group, and a free CDDP group, with 3 mice in the PBS group, 12 mice in the nanoparticle group, and 12 mice in the free CDDP group; respectively injecting them with 200 μL of a nanoparticle solution and 200 μL of a free CDDP solution via the caudal vein at an injection dose of 5 mg/kg (calculated according to the concentration of Pt element), with the drug administered every other day, 3 times in total; after all the drugs were administered, collecting blood samples from the retroorbital venous plexus of mice by eyeball enucleation on the 7th, 14th, 21st and 28th day after the administration, with eyeball blood also collected on the 28th day in the PBS group; making the collected blood samples stay in a refrigerator at 4° C. overnight, then centrifuging them with a centrifuge at 1000 r/min for 5 min, and then taking out the upper serum; and analyzing the levels of the liver function indexes including aspartate aminotransferase (AST), alkaline phosphatase (ALP) and alanine aminotransferase (ALT), as well as the renal function indexes including urea and creatinine (Crea) in the serum with a blood biochemical analyzer. The results were shown in FIG. 10. It could be found that there was no significant difference between the nanoparticle administration group and the control group (PBS group) in terms of the liver and kidney indexes, indicating that there was no obvious injury to the liver and kidney functions; however, in the free CDDP group, the liver indexes changed greatly and the kidney indexes Urea and Crea increased rapidly, indicating that CDDP had certain toxicity to the kidney. In conclusion, it could be seen from the measurement results of biochemical indexes that the nanoparticle drug of the present invention had no obvious toxic side effects on the liver and kidney, having broad clinical application prospects.

Example 2: When the protein nanoparticles were prepared, the pH was adjusted to 5.0 and 6.0, respectively (the pH was 5.5 in Example 1), with the other steps being the same as those in Example 1, thus obtaining the nanoparticles with a TEM size of 4.5-5.3 nm (this size, due to the heavy atom effect, only reflected the size of the area where the platinum atom of the nanoparticle core was located, the same below).

Example 3: During preparation of the protein nanoparticles, the molar ratio of platinum element to Ce6 was adjusted to 1:1 and 8:1, respectively (the molar ratio of Pt to Ce6 was 4:1 in Example 1), with the other conditions being the same as those in Example 1, thus obtaining the Pt/Ce6 protein nanoparticles with good stability having a TEM size of 4.2-4.9 nm.

During preparation of the protein nanoparticles, the molar ratio of platinum element to Ce6 was adjusted to 1:2 (the molar ratio of Pt to Ce6 was 4:1 in Example 1), with the other conditions being the same as those in Example 1; and the solution after the reaction was turbid, and the Pt/Ce6 protein nanoparticles with good stability could not be obtained.

Example 4: During preparation of the protein nanoparticles, the reaction temperature was adjusted to 25° C. and 37° C., respectively (the reaction temperature was 55° C. in Example 1), with the other conditions being the same as those in Example 1, thus obtaining the Pt/Ce6 protein nanoparticles with good stability having a TEM size of 4.2-5 nm.

Example 5: The reaction time during the preparation of platinum sulfide protein nanoparticles in Example was adjusted to 1 and 8 h, respectively (the reaction time was 4 h in Example 1), with the other conditions being the same as those in Example 1; when the reaction time was 1 h, Pt/Ce6 protein nanoparticles with good stability could be obtained, having a TEM size about 5 nm; and when the reaction time was 8 h, the solution after the reaction was turbid, and the Pt/Ce6 protein nanoparticles with good stability could not be obtained.

Using HSA as a protein template, the present invention prepared nanoparticles Pt/Ce6@HSA by co-precipitating in an albumin cavity the platinum-based chemotherapeutic drug and the photosensitizer Ce6, which were difficult to be loaded directly, see FIG. 1I, thus realizing co-loading and combined application of chemotherapy and photodynamic therapy in tumor treatment, which laid a foundation for further research on the clinical application. In the preparation of nanoparticles, drug-loaded protein nanoparticles with a smaller particle size, better dispersion and regular morphology were successfully obtained. The existence of divalent platinum and the successful coordination of platinum with a carboxyl group were proved by characterization with XPS, EDX, FTIR and the like. The nanoparticles had good photostability and chemical stability, as well as good capability to generate singlet oxygen. In addition, the results of the release rule study showed that the nanoparticles had a certain sustained-release effect and were conducive to reaching the tumor site to play a role.

In the study on the anti-tumor effect of nanoparticles, the experimental results at the cellular level showed the following indications: The uptake of nanoparticles by tumor cells was significantly increased in a time-dependent manner; with the ingested nanoparticles mainly located in the lysosome, after irradiation, a large amount of ROS was produced in the cell, causing the lysosome to rupture, thus promoting the further transport of drugs into the cytoplasm and nucleus, thereby realizing the synergistic effect of chemotherapy and photodynamic therapy, as shown in FIG. 12; the MTT experiment showed that the combination therapy with the nanoparticles effectively improved the anti-tumor effect, and the drugs had strong photodynamic effect and chemotherapy effect, reflecting the advantages of the combination of chemotherapy and photodynamic therapy; the results of the EdU staining test of cell proliferation showed that the nanoparticles could significantly inhibit the proliferation of tumor cells, with the inhibition effect significantly enhanced after irradiation, which further confirmed the anti-tumor effect of nanoparticles; and as shown by the results of apoptosis, mitochondrial membrane potential staining, a platinum-DNA adduct and the Western blot experiment, the mitochondrial membrane potential decreased after treatment with the nanoparticles, and after irradiation, the potential decreased significantly, the apoptosis level increased significantly, the adduct production increased, and the expression of apoptosis-related proteins changed significantly, which further proved the advantages of nanoparticles combining the two therapies.

As indicated by the results of evaluating the anti-tumor effects in mice, the nanoparticles had prolonged elimination half-life and better long-circulating capacity; the nanoparticles had good tumor targeting; after targeting the tumor site, the nanoparticles could effectively generate reactive oxygen and had a good PDT effect: after combining chemotherapy and photodynamic therapy, the nanoparticles could significantly inhibit the growth and metastasis of tumor in mice; the results of section staining showed that the nanoparticles could significantly injure tumor cells and inhibit tumor proliferation, which proved the advantages of combined treatment; and the nanoparticles could be discharged from the body through biological metabolism in mice, had no long-term toxicity, did no significant injury to liver and kidney, and had high biosafety.

To sum up, the present invention ingeniously designs and successfully prepares a platinum-based drug/photosensitizer-loaded protein nanoparticle that combines chemotherapy and photodynamic therapy, the nanoparticle producing a synergistic anti-tumor effect and having a remarkable tumor inhibition effect.

The invention claimed is:

1. A platinum-based drug and photosensitizer-loaded protein nanoparticle, comprising a platinum-based drug/photosensitizer complex, and a protein encapsulating the platinum-based drug-/photosensitizer complex, wherein the protein is albumin, the platinum-based drug is a diammine dihydrate platinum ion, and the photosensitizer is chlorin e6.

2. A preparation method for the platinum-based drug and photosensitizer-loaded protein nanoparticle according to claim 1, comprising the following steps: adding a solution of chlorin e6 to a mixed solution of the diammine dihydrate platinum ion and protein, reacting, and then carrying out centrifugal ultrafiltration to obtain the platinum-based drug/photosensitizer-loaded protein nanoparticles.

3. The preparation method for the platinum-based drug and photosensitizer-loaded protein nanoparticle according to claim 2, wherein: a ratio of the protein to the diammine dihydrate platinum ion to the chlorin e6 is 100 mg:(20-50 μmol):(3-15 μmol).

4. The preparation method for the platinum-based drug and photosensitizer-loaded protein nanoparticle according to claim 3, wherein: the ratio of the protein to the diammine dihydrate platinum ion to the chlorin e6 is 100 mg:(25-40 μmol):(5-10 μmol).

5. The preparation method for the platinum-based drug and photosensitizer-loaded protein nanoparticle according to claim 2, wherein: the solution of chlorin e6 is added to the mixed solution of the diammine dihydrate platinum ion and protein, the pH is adjusted to 4.0-8.0, and then reaction is carried out at 25° C.-60° C. for 1-8 h; and the speed of centrifugal ultrafiltration is range from 1500 r/min to 4000 r/min.

6. The preparation method for the platinum-based drug and photosensitizer-loaded protein nanoparticle according to claim 5, wherein: the pH of the mixed solution is adjusted to 5.0-6.5; and an upper limit of the molecular weight of the substance retained during the centrifugal ultrafiltration is 100 kD.

* * * * *